US006180820B1

United States Patent
Jawaid et al.

(10) Patent No.: US 6,180,820 B1
(45) Date of Patent: Jan. 30, 2001

(54) PROCESS FOR THE PRODUCTION AND PURIFICATION OF N-BUTYL ACRYLATE

(75) Inventors: Mahmood Nayyer Azam Jawaid, Houston; Douglas Edward Schepp, Highland Village, both of TX (US)

(73) Assignee: Celanese International Corporation, Dallas, TX (US)

( * ) Notice: Under 35 U.S.C. 154(b), the term of this patent shall be extended for 0 days.

(21) Appl. No.: 09/395,891

(22) Filed: Sep. 14, 1999

(51) Int. Cl.$^7$ .............................. C07C 67/48; C07C 69/52

(52) U.S. Cl. ........................................... 560/218; 560/205

(58) Field of Search ...................................... 560/205, 218

(56) References Cited

U.S. PATENT DOCUMENTS 5,877,345 * 3/1999 Bauer et al. ......................... 560/218

* cited by examiner

Primary Examiner—Shailendra Kumar
Assistant Examiner—J. Parsa
(74) Attorney, Agent, or Firm—M. Susan Spiering

(57) ABSTRACT

A process for the production of n-butyl acrylate (BuAcA) including the steps of esterifying acrylic acid (HAcA) with a n-butanol (n-BuOH) in a reaction zone, obtaining a condensate from the overhead vapors from the reaction zone which separates into organic and aqueous phases, feeding the organic phase comprising a major portion of BuAcA and minor portions of BuOH, water and light ends impurities to a finishing fractionation zone from which is obtained a side stream of a finished high purity BuAcA and an overhead condensate comprising BuAcA, BuOH, water, and light ends, recycling most of the overhead condensate from the finishing zone to the reaction zone, feeding the remainder of such condensate to a purge recovery zone together with a stream of makeup water, obtaining an overhead condensate from the purge recovery zone which separates into organic and aqueous phases each containing a portion of light ends produced in the reaction, recycling a portion of the organic phase as reflux to the purge recovery zone and discarding the remainder, and recycling at least a portion of the aqueous phase as feed to the purge recovery zone and discarding any remainder. Discarding of portions of the two phases of the overhead condensate has the effect of preventing or retarding the buildup of light ends in the system, while the amounts of water in the water makeup stream and the recycled portion of the aqueous phase of the overhead condensate to the purge recovery zone forms low-boiling azeotropes with components of the light ends thus facilitating separation of the light ends from the BuAcA and BuOH in the purged portion of the finishing zone overhead.

12 Claims, 1 Drawing Sheet

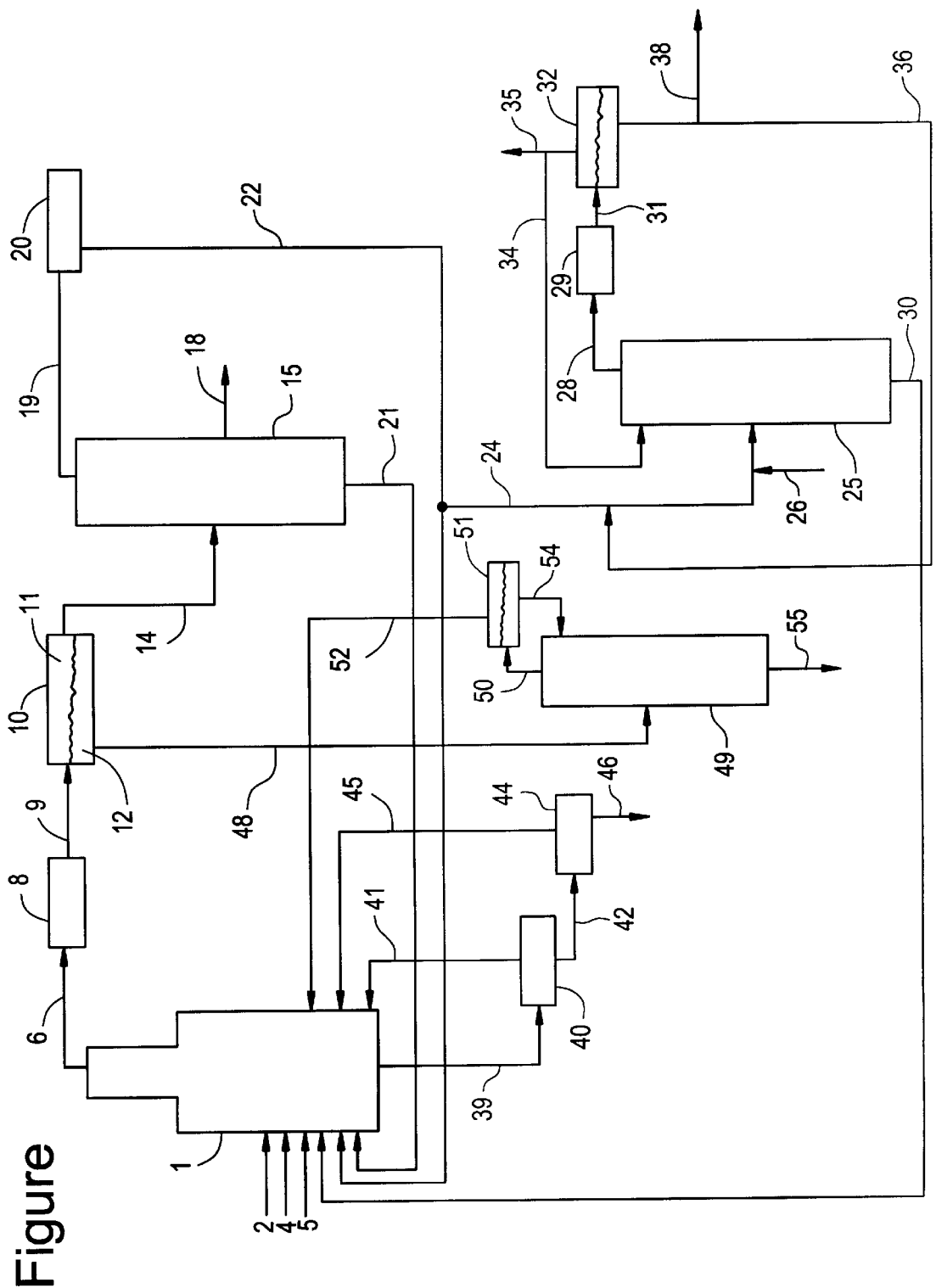
Figure

PROCESS FOR THE PRODUCTION AND PURIFICATION OF N-BUTYL ACRYLATE

BACKGROUND OF THE INVENTION

1. Field of the Invention

The invention relates to an improved process for the production and purification of nbutyl acrylate.

2. Background Information and Description of Related Art n-Butyl acrylate (BuAcA) is a commodity chemical useful for the production of acrylic resins and polymers and copolymers for paint formulations, solvent coatings, textile and leather finishes and adhesives and binders. One method of synthesizing BuAcA is to react n-butanol (BuOH) with acrylic acid (HAcA) in the presence of an acid catalyst, e.g., a sulfonic acid, in at least one reaction zone to produce a mixture of BuAcA, water and several by-product impurities, and subjecting the product mixture to purification in at least one distillation zone, together with any of various schemes of reflux and recycle streams among the reaction zone(s) and distillation zone(s) to obtain a BuAcA of relatively high purity. When any of these processes are operated, low boiling impurities produced in the reaction zone, i.e., those having boiling points near or below BuAcA, such as butyl acetate and dibutyl ether and characterized as "light ends," or "lights" must be systematically disposed of to prevent them from interfering with the described reaction and compromising the purity of the BuAcA. However, this is often difficult to accomplish, e.g. by purging an appropriate stream, without also losing an unduly large amount of BuAcA product and unreacted BuOH, and/or incurring an unfavorably large cost in energy consumption or purification equipment to prevent such loss. Thus, any improved process, which accomplishes an adequate disposal of light ends while keeping the loss of BuAcA and unreacted BuOH and/or the incremental cost of energy and equipment to a minimum, is very desirable.

U.S. Pat. No. 4,012,439, issued Mar. 15, 1977 to Erpenbach et al., discloses a process for producing n-butyl acrylate by reacting acrylic acid with n-butanol in liquid phase and in contact with an acid cation exchanger as a catalyst. The process utilizes a single reaction zone and three distillation zones.

U.S. Pat. No. 4,280,010, issued Jul. 21, 1981 to Erpenbach et al., discloses a continuous process for making alkyl acrylates free from ether by reacting a $C_1$–$C_4$-alkanol in a molar ratio of 1:1 to 1:2 in liquid phase at 80° to 130° C. under 100–760 mmHg in the presence of a catalyst. The process employs a single reaction zone and two distillation zones for separating the alkyl acrylate from unreacted alkanol and ether by-product.

U.S. Pat. No. 4,814,493, issued Mar. 21, 1989 to Dougherty et al., teaches a process for the production of a n-butyl acrylate by reaction of n-butanol with acrylic acid in the presence of an esterification catalyst and soluble manganese or cerium. The system for carrying out the process includes a reactor from which a butyl acrylate reaction product is sent to a finishing tower wherein the reaction product is separated into a pure butyl acrylate stream, a volatile stream a portion of which is sent to a butanol recovery tower, and a residue stream which is recycled to the reactor. A butanol stream from the butanol recovery tower is recycled to the reactor, and a residue stream from such tower is removed from the system.

South African Patent No. 9704628 issued Mar. 25, 1998, discloses a process wherein acrylic acid (HAcA) and n-butanol (BuOH) are reacted in two reactors in series, and the product separated in two distillation columns to produce a stream comprising butyl acrylate (BuAcA), dibutyl ether (DBE), butyl acetate (BuAc), and BuOH. Such stream is further separated in a splitter distillation column to provide an overhead fraction containing DBE, BuAc, and BuOH, and a bottoms fraction containing BuAcA and heavy end components ("heavies"), e.g., low molecular weight polymers of HAcA and/or BuAcA and Michael addition products. The overhead fraction from the splitter column is subjected to further distillation in the presence of water to separate BuOH and BuAcA from lights containing DBE and BuAc, with the BuOH and BuAcA being recycled to either or both reactors and the lights being sent to waste treatment, while the bottoms fraction from the splitter distillation is rectified in a butyl acrylate distillation column to separate BuAcA product from heavies which are recycled to either or both reactors.

BRIEF SUMMARY OF THE INVENTION

In accordance with this invention, n-butyl acrylate (BuAcA) is produced by a process comprising reacting generally, amounts of n-butanol (BuOH) with acrylic acid (HAcA) in a reaction zone from which an overhead vapor mixture is withdrawn comprising BuAcA, BuOH, water and light ends which are organic by-product impurities having boiling points near or somewhat below that of BuAcA, and composed mainly of n-butyl acetate (BuAc) and di-n-butyl ether (DBE). BuAcA, BuOH and water are removed in the overhead vapor mixutre by a combination of binary and ternary azeotropes. The vapor mixture is condensed to form a substantially organic liquid phase comprising a major proportion of BuAcA and minor proportions of BuOH, water and light ends, and a substantially aqueous liquid phase comprising mainly water and a minor proportion of BuOH. The organic phase is fed to a finishing fractionation zone, from which a side stream of BuAcA product is withdrawn. Most of the overhead stream of the finishing fractionation zone composed of a portion of the total of BuAcA and BuOH present and minor portions of water and light ends, is recycled to the reaction zone. However, to prevent an undesirable buildup of light ends in the system, a minor proportion of such overhead stream is purged and sent to a purge recovery fractionation zone together with a quantity of makeup water such that the formation of low boiling azeotropes of water with components of the light ends is increased thus facilitating separation of the light ends from the valuable BuAcA and BuOH in the purge stream.

The overhead vapors from the purge recovery fractionation zone are condensed to form separate organic and aqueous liquid phases, with each phase containing a portion of the light ends produced in the system. The majority of light end impurities remain in the organic phase compared to the aqueous phase. A portion of the organic phase and optionally, a portion of the aqueous phase, are discarded such that the total amount of light ends in such discarded portions is comparable to the amount of light ends produced in the reaction. By "discard" what is meant is to remove the stream or portion thereof from the process. The stream may be further processed for proper disposal or further treated for recovery and reuse. The remainder of the organic phase is recycled as reflux to the purge recovery zone and at least a portion of the aqueous phase is recycled as feed to the purge recovery zone.

The residue from the purge recovery zone, containing the bulk of the BuAcA and BuOH in the purged portion of the organic phase of the condensed overhead from the finishing zone, and having a reduced light ends content is recycled to the reaction zone.

The process of the invention accomplishes the prevention of a buildup of light ends in the system while minimizing the loss of BuAcA and unreacted BuOH, while keeping the cost of energy and new equipment to accomplish this purpose, at a relatively low level.

BRIEF DESCRIPTION OF THE DRAWING

The drawing is a schematic representation of a preferred embodiment of the overall process of this invention.

DETAILED DESCRIPTION OF THE INVENTION

In the synthesis of n-butyl acrylate (BuAcA) in accordance with this invention, close to equimolar amounts of acrylic acid (HAcA) and n-butanol (BuOH) are fed to the reaction zone together with an acid esterification catalyst, e.g., about 1 to about 5 wt % based on the weight of total reaction mixture. Examples of the esterification catalyst include alkyl- or arylsulfonic acid such as methanesulfonic, benzenesulfonic or toluenesulfonic acid. Close to equimolar amounts of HAcA and BuOH are fed to the reaction zone e.g. about 0.85 to about 1.3 moles of BuOH per mole of HAcA. Stoichiometric excess of BuOH over HAcA is preferable to minimize the polymerizable free HAcA in the system, e.g. about 0.99 to about 1.3 moles of BuOH per mole of HAcA. To minimize polymerization in the process, a polymerization inhibitor is preferably also fed and may be mixed with the HAcA. Those of skill in the art will appreciate the type and amount of inhibitor necessary to achieve non-polymerization, said type and amount being based on a variety of factors. The inhibitor may be, for example, phenothiazine or a phenolic compound such as a dihydroxybenzene or a mono-lower alkyl dihydroxybenzene, e.g. hydroquinone or its monomethyl or monoethyl ether.

In an embodiment of the invention, the esterification of HAcA with BuOH to produce BuAcA takes place primarily in the base reaction portion of the reaction vessel with the top portion of the vessel containing fractionation stages, e.g. in the form of trays and bubble caps or packing, to separate the bulk of the BuAcA and unreacted BuOH from residue at the base of the column comprising primarily low molecular weight polymers of HAcA and BuAcA, catalyst and polymerization inhibitor. Also remaining in the reactor are some quantities of free HAcA and BuAcA. The reactor vessel operates at a temperature, e.g., in the range of about 20 to about 150° C. and a pressure in the range of about 50 to about 400 mmHgA.

The overhead vapors from the reaction vessel consist mainly of BuAcA, lower amounts of BuOH and water and a minor amount of light ends, i.e. by-product organic compounds having somewhat lower boiling points than BuAcA, such as n-butyl acetate (BuAc), n-butyl propionate (BuPr), DBE, secondary butyl acrylate (SBuAcA) and isobutyl acrylate (IBuAcA). The overhead vapors are condensed and separated into two phases, a substantially organic phase having a major portion of BuAcA, reduced amounts of BuOH and water and the light ends, and a substantially aqueous phase comprising mainly water and BuOH. The organic phase is sent to the finishing fractionization zone (the finishing tower) and the aqueous phase to a butanol recovery zone (the butanol recovery tower) wherein the BuOH is separated from the water for recycle to the reaction vessel.

The residue from the reaction vessel comprising mainly low molecular weight polymers of HAcA and BuAcA, some free HAcA, BuOH, catalyst and inhibitor is fed to a heat treater operating at a temperature, e.g., of about 150 to about 250° C. and a pressure, e.g., of about 80 to about 150 psig, where some of the polymers are converted to the monomers. See Horlenko, U.S. Pat. No. 3,868,410 for further discussion regarding heavy end components. After a residence time of, e.g., about 1 to about 50 min, most of the heat treated residue is recycled back to the reaction vessel, with a slip stream, e.g., of about 5 to about 20 wt % of the heat treated residue being removed to a heavy ends removal distillation unit, operating at a temperature of about 125 to about 200° C. and a pressure of about 100 to about 700 mmHgA. The volatiles from the heavy ends removal unit are recycled to the reaction vessel while the residue from such unit is discarded.

The organic phase of the overhead condensate from the reaction vessel comprises a major amount, e.g., about 80 to about 95 wt % of BuAcA, and minor amounts, e.g., about 5 to about 15 wt % of BuOH, about 1 to about 3 wt % water, about 1 to about 10 wt % of light ends, and about 0.001 to about 0.05 wt % of HAcA, is fed to the finishing tower, such tower operating at a temperature, e.g., of about 20 to about 150° C. and a pressure, e.g., of about 50 to about 400 mmHgA. Finished BuAcA having a purity of, e.g., about 99.0 to about 99.99 wt % is withdrawn as a vapor side stream from the finishing tower, and overhead vapors comprising, e.g., about 10 to about 80, preferably about 35 to about 70 wt % of BuAcA, e.g., about 10 to about 80 wt %, preferably about 25 to about 70 wt % of BuOH, and e.g., about 1 to about 10 wt % of light ends, are withdrawn from the top of the finishing tower. The overhead vapors from the finishing tower are condensed and a portion of the condensate, e.g., from greater than about 0 to about 75 wt %, preferably about 5 to about 50 wt % is purged and sent to a purge recovery fractionation zone (the purge recovery tower) with the remainder being recycled to the reaction vessel. Here, "greater than about 0" means at least a small quantity which is large enough or sufficient to operate the purge recovery tower. The residue from the finishing tower contains a major amount of BuAcA and is recycled to the reaction vessel.

The aqueous phase of the reaction vessel overhead condensate containing, e.g., about 1 to about 10 wt % of BuOH, and about 90 to about 99 wt % of water, is fed to the butanol recovery tower operating at a temperature, e.g., of about 70 to about 120° C. and a pressure, e.g., of about 1 to about 5 psig. Alternatively the aqueous phase of the reaction vessel overhead condensate may be discarded. The vapors from the top of the tower are primarily a binary azeotrope of BuOH and water which is condensed into two immiscible phases, one being predominantly BuOH which is recycled to the reaction vessel and the other a solution of a minor amount of BuOH in water which is recycled to the butanol recovery tower as reflux or discarded or recycled to the reaction vessel. The residue from the tower is composed primarily of water containing very little BuOH and is discarded.

The purged portion of the finishing tower overhead condensate contains an amount of light ends which, when discarded, is sufficient to prevent an undesirable buildup of light ends in the system. However, to minimize wastage of BuOH and HAcA utilized in the process, the purge stream is azeotropically distilled in the purge recovery tower to separate a major portion of BuOH and BuAcA from the light ends. More specifically, the purge recovery tower operates at a temperature, e.g., of about 30 to about 150° C., preferably about 65 to about 110° C., a subatmospheric pressure of, e.g., about 50 to about 500 mmHgA, preferably about 200 to about 350 mmHgA. The primary feed to the purge recovery tower is the purged portion of the finishing tower overhead condensate, described previously. Also entering the purge recovery tower is a portion of the substantially organic phase of the overhead condensate as reflux and in many cases a portion of the aqueous phase of the overhead condensate as recycle, both to be described in greater detail hereinafter; and a makeup supply of water. The water in the recycled aqueous phase of the overhead condensate and the makeup water aid in the azeotropic distillation of the light ends in the feed to separate them from the BuOH and BuAcA in such feed.

The overhead vapors from the purge recovery tower are condensed and the condensate separated into organic and aqueous phases, with the organic phase being, e.g., about 70 to about 95 wt % of the total overhead stream and containing, e.g., about 20 to about 60 wt % of BuOH, about 10 to about 60 wt % BuAcA, about 5 to about 20 wt % of light ends, and about 5 to about 10 wt % of water. The aqueous phase from the condensed vapors make up the remainder of the total overhead containing, e.g., about 85 to about 98 wt % of water, about 2 to about 15 wt % of BuOH, and generally less than about 1.0 wt % of light ends. As previously mentioned, a portion of the condensate organic phase, e.g., about 10 to about 80 wt %, is recycled to the purge recovery tower as reflux, the remainder being discarded, and at least a portion of the condensate aqueous phase, e.g. about 50 to about 100 wt %, is recycled to the purge recovery tower as feed, with any remainder of this stream also being discarded. The amount of water in the recycled aqueous phase is correlated with the amount of water in the makeup stream being fed to the tower such that the total amount of water in the condensate aqueous phase and in the makeup stream is, e.g., from about 0 to about 50 wt %, preferably from about 1 to about 40 wt %, most preferably about 5 to about 20 wt % of the organic feed going to the tower. It has been determined that this amount of water aids in the separation of light ends from the BuOH and BuAcA in the streams entering the tower by forming low boiling azeotropes with components of the light ends, particularly BuAc and DBE.

The purge recovery tower is operated such that the total amount of the light ends in the discarded portions of the overhead condensate organic and aqueous phases is comparable to the amount of light ends produced in the system so that there is no undesirable buildup of light ends in the system.

The residue composition from the purge recovery tower contains from about 10 to about 80 wt % of BuAcA and about 10 to about 80 wt % of BuOH, as well as relatively smaller amounts of water and light ends, and is recycled to the reaction vessel.

The process of the invention may be further described with reference to the drawing, which is a schematic diagram of a preferred embodiment of the inventive process. Into reaction vessel 1 are fed n-butanol (BuOH), acrylic acid (HAcA), and an acid esterification catalyst such as methanesulfonic acid (MSA) tirough lines 2, 4, and 5 respectively. A polymerization inhibitor is also typically employed throughout the process, and added at appropriate locations and appropriate concentrations. Those of skill in the art will recognize appropriate locations and concentrations to utilize. Conditions of temperature and pressure are maintained in reaction vessel 1 to cause a reaction of HAcA and BuOH present in some excess to form n-butyl acrylate (BuAcA) and water, and small amounts of various by-products such as light ends including n-butyl acetate (BuAc) and di-n-butyl ether (DBE) and heavy ends such as low molecular weight polymers of HAcA and BuAcA. Vapors of the more volatile compounds present including BuOH, BuAcA, water and light ends rise into the fractionization zone situated immediately above the reaction zone of reaction vessel 1. These vapors are forwarded through line 6 into condenser 8 from which the liquid condensate flows through 9 into separator 10 where the condensate is separated into immiscible substantially organic phase 11 and aqueous phase 12. The organic phase condensate containing predominately BuAcA is fed through line 14 to finishing tower 15 from which high purity finished BuAcA is withdrawn as a sidestream through line 18. The overhead vapors from tower 15 containing significant amount of BuOH and BuAcA and lesser amounts of water and light ends, are fed through line 19 to condenser 20, and the residue from tower 15 containing primarily BuAcA is recycled through line 21 to reaction vessel 1. The diagram indicates stream 21 forwarded to the base of vessel 1. Those of skill in the art will appreciate that this stream may be forwarded to any location in 1 as appropriate. Most of the condensate from condenser 20 is recycled through line 22 to reaction vessel 1. However, a minor portion of the condensate is purged and fed through line 24, to purge recovery tower 25 together with a supply of makeup water through line 26. The addition of makeup water acts to keep the content of water in purge recovery tower sufficient to form water azeotropes with various of the light ends and render more efficient the separation of the light ends in purge recovery tower 25. The overhead vapors from purge recovery tower 25 containing significant amounts of BuOH, water, light ends, and BuAcA are fed through line 28 to condenser 29. The residue of tower 25 containing significant amounts of BuAcA and BuOH is stripped of light ends and is recycled through line 30 to reaction vessel 1. The condensate from condenser 29 is fed through line 31 to separator 32 where it separates into organic and aqueous phases. A part of the organic phase is recycled through line 34 to purge recovery tower 25 as reflux while the remainder is withdrawn through line 35 and discarded. Similarly, a part of the aqueous phase is recycled through line 36 to purge recovery tower 25 and the remainder withdrawn through line 38 and discarded. The foregoing discarding of portions of the organic and aqueous phases from separator 32 act to keep the light ends of the overall system in balance.

The residue from reaction vessel 1 comprising mainly low molecular weight polymers of HAcA and/or BuAcA and Michael addition products is fed through line 39 to heat treater 40 where part of the heavies are converted to HAcA and/or BuAcA. Most of the heat-treated stream from heat treater 40 containing increased amounts of HAcA and/or BuAcA is recycled through line 41 to reaction vessel 1. However, to prevent a build up of heavy ends in the system, a slip stream from the heat treater 40 is fed through line 42 to a heavy ends removal unit 44. The vapors from unit 44 containing a significant amount of HAcA and/or BuAcA are condensed and recycled through line 45 to reaction vessel 1 while the residue from unit 44 are withdrawn through line 46 and discarded.

Aqueous phase 12 from separator 10 containing some BuOH is fed through line 48 to an intermediate point of butanol recovery tower 49. Optionally, stream 48 may be discarded. The overhead vapors from 49 comprising an azcotrope of BuOH with water is fed through line 50 to condenser receiver 51 where it separates into an organic phase comprising an increased amount of BuOH which is recycled to reaction vessel 1 through line 52, and an aqueous phase comprising some amount of BuOH which is either fed as reflux to butanol recovery tower 49 through line 54 or alternatively, is discarded or recycled to the reaction vessel.

The residue containing predominantly water is withdrawn through line 55 and discarded.

What is claimed is:

1. A process for producing n-butyl acrylate (BuAcA) comprising:
   (a) esterifying acrylic acid (HAcA) with n-butanol (BuOH) in a reaction zone from which an overhead vapor mixture is withdrawn, said vapor mixture containing BuAcA, BuOH, water and light ends components, said light ends components having boiling points near or somewhat lower than that of BuAcA,
   (b) condensing said vapor mixture to form an organic phase containing BuAcA, BuOH, light ends, and an aqueous phase containing predominantly water and BuOH,
   (c) feeding said organic phase to a finishing fractionation zone,
   (d) withdrawing BuAcA having a high degree of purity from said finishing zone,
   (e) withdrawing and condensing the overhead vapors from said finishing zone comprising a major portion of the total of BuAcA and BuOH present and minor portions of water and light ends,
   (f) recycling a major portion of said overhead condensate of the finishing zone to the reaction zone,
   (g) feeding a minor portion of said overhead condensate of the finishing zone together with a stream of makeup water, to a purge recovery fractionation zone,
   (h) condensing the overhead vapors of said purge recovery zone comprising significant amounts of BuOH, BuAcA, water and light ends to form an organic phase containing BuOH, BuAcA, and lights ends and an aqueous phase containing some BuOH, BuAcA and light ends,
   (i) recycling a portion of said organic phase of the overhead condensate from the purge recovery zone back to said purge recovery zone as reflux,
   (j) discarding the remainder of said organic phase,
   (k) recycling at least a portion of said aqueous phase of the overhead condensate of the purge recovery zone as feed to the purge recovery zone, with any remainder being discarded, wherein,
   the total amount of water in said recycled portion of the aqueous phase of the overhead condensate of the purge recovery zone and said makeup stream of water having the effect of increasing the formation of low boiling azeotropes with the components of light ends entering the purge recovery zone.

2. The process of claim 1 wherein said overhead condensate from the finishing zone comprises about 10 to about 80 wt % of BuAcA, about 10 to about 80 wt % of BuOH and about 1 to about 10 wt % of light ends.

3. The process of claim 2 wherein said range of BuAcA is about about 35 to about 70 wt % and said range of BuOH is about 25 to about 70 wt %.

4. The process of claim 1 wherein from greater than about 0 to about 75 wt % of said overhead condensate from the finishing zone is fed to said purge recovery zone with the remainder of said condensate being recycled to the reaction zone.

5. The process of claim 4 wherein the amount of said overhead condensate from the finishing zone fed to the purge recovery zone is about 5 to about 50 wt %.

6. The process of claim 1 wherein said purge recovery zone operates at a temperature in the range of about 30 to about 150° C., and a pressure in the range of about 50 to about 500 mmHgA.

7. The process of claim 6 wherein said range of temperatures in the purge recovery zone is about 65 to about 110° C. and said range of pressures in said zone is about 200 to about 350 mmHgA.

8. The process of claim 1 wherein said organic phase of the overhead condensate of the purge recovery zone is about 70 to about 95 wt % of the total condensate and contains about 20 to about 60 wt % of BuOH, about 10 to about 60 wt % BuAcA and about 5 to about 20 wt % light ends, with about 10 to about 80 wt % of said organic phase being recycled to said purge recovery zone as reflux and the remainder being discarded.

9. The process of claim 8 wherein said aqueous phase of the overhead condensate of the purge recovery zone contains about 2 to about 15 wt % of BuOH, and less than about 1.0 wt % of light ends with about 50 to about 100 wt % of said aqueous phase being recycled as feed to said purge recovery zone and the remainder being discarded, the amount of light ends in the discarded portions of said organic and aqueous phases of the overhead condensate of the purge recovery zone being such as to prevent or retard the buildup of light ends in the system.

10. The process of claim 1 wherein the total of the water in the makeup stream of water to the purge recovery zone and the recycled portion of the aqueous phase of the overhead condensate of the purge recovery zone are correlated such that the total amount of water in the two streams is in the range of from about 0 to about 50 wt % of all the streams being fed to the purge recovery zone.

11. The process of claim 10 wherein said range of water is about 5 to about 20 wt %.

12. The process of claim 1 wherein the residue from said purge recovery zone comprising a major amount of the total of BuAcA and BuOH present and largely stripped of light ends is recycled to said reaction zone.

* * * * *